(12) United States Patent
Colgan et al.

(10) Patent No.: US 6,648,902 B2
(45) Date of Patent: Nov. 18, 2003

(54) FIBEROPTIC LIGHTING ACCESSORY

(75) Inventors: Diane L. Colgan, Potomac, MD (US); James H. Layer, Cooper City, FL (US); Kenneth Solovay, Weston, FL (US); Tom Jacobs, Fort Lauderdale, FL (US)

(73) Assignee: GMP Surgical Solutions, Inc., Ft. Lauderdale, FL (US)

( * ) Notice: Subject to any disclaimer, the term of this patent is extended or adjusted under 35 U.S.C. 154(b) by 0 days.

(21) Appl. No.: 09/910,191

(22) Filed: Jul. 20, 2001

(65) Prior Publication Data

US 2002/0035312 A1 Mar. 21, 2002

Related U.S. Application Data

(60) Provisional application No. 60/275,972, filed on Mar. 15, 2001, and provisional application No. 60/219,960, filed on Jul. 20, 2000.

(51) Int. Cl.[7] ............................................... A61B 17/28
(52) U.S. Cl. .................... 606/205; 606/16; 606/151; 606/206; 600/218; 600/223
(58) Field of Search .................... 606/205–209, 606/13–16, 151, 167, 170; 600/218, 223, 239, 245; 604/104–109; 358/118

(56) References Cited

U.S. PATENT DOCUMENTS

| 2,376,448 A | 5/1945 | Neugass | 128/354 |
|---|---|---|---|
| 3,287,547 A | 11/1966 | Spedding | 240/6.46 |
| 3,614,414 A | 10/1971 | Gores | 240/2 |
| 4,096,864 A | 6/1978 | Kletschka et al. | 128/354 |
| 4,165,746 A | 8/1979 | Burgin | |
| 4,671,283 A | 6/1987 | Hoskin et al. | 128/354 |
| 5,190,028 A * | 3/1993 | Lafferty et al. | 128/6 |
| 5,250,046 A | 10/1993 | Lee | |
| 5,318,589 A | 6/1994 | Lichtman | |
| 5,342,375 A | 8/1994 | Lemole | 606/148 |
| 5,569,300 A * | 10/1996 | Redmon | 606/207 |
| 5,665,100 A * | 9/1997 | Yoon | 606/170 |
| 5,667,473 A | 9/1997 | Finn et al. | |
| 5,667,478 A | 9/1997 | McFarlin et al. | 600/182 |
| 5,868,668 A | 2/1999 | Weiss | |
| 5,916,149 A | 6/1999 | Ryan, Jr. | |
| 6,129,662 A | 10/2000 | Li et al. | 600/182 |
| 6,176,824 B1 * | 1/2001 | Davis | 600/178 |
| 6,185,356 B1 | 2/2001 | Parker et al. | |

FOREIGN PATENT DOCUMENTS

| DE | 42 34 050 A1 | 6/1993 |
|---|---|---|
| WO | WO 90/10420 | 9/1990 |
| WO | WO 99/01696 | 1/1999 |

* cited by examiner

Primary Examiner—Linda C. M. Dvorak
Assistant Examiner—A. Farah
(74) Attorney, Agent, or Firm—Banner & Witcoff, Ltd.

(57) ABSTRACT

A lighting accessory stem using fiberoptic illumination is provided. In certain embodiments, the lighting accessory system is combinable with a hand tool, for example a forceps, to illuminate the grasping tips of the tool. The lighting accessory system provides an illuminable tool whereby an object may be illuminated and grasped while being illuminated without obstruction by the illumination means. In certain embodiments, the lighting accessory system may be used for medical or surgical tools.

42 Claims, 10 Drawing Sheets

FIBEROPTIC LIGHTING ACCESSORY

CROSS REFERENCE TO RELATED APPLICATIONS

This application claims priority to U.S. Provisional Application No. 60/219,960, filed Jul. 20, 2000, and U.S. Provisional Application No. 60/275,972, filed Mar. 15, 2001. The disclosures of each of these applications is incorporated herein by reference.

FIELD OF THE INVENTION

In one aspect, the present invention relates to a lighting accessory system for providing an illuminable tool. More particularly, the present invention relates to a fiberoptic lighting accessory affixable to a surgical or medical tool.

BACKGROUND OF THE INVENTION

Practitioners in the surgical arts frequently find themselves with a need for enhanced visualization of a body tissue or other workpieces disposed within body cavities. A variety of illumination systems have been devised to address this need. One option is overhead lighting. Overhead illumination in an operating room is directable, and in some cases focusable, so that a surgeon may use this lighting better to visualize the surgical field. Overhead light sources, however, provide a more general and diffuse type of illumination. Another option involves the use of illuminated devices held in a person's hand. To direct light towards a specific target, surgeons and other operating room personnel may employ handheld lighting instruments, such as lighted retractors or flexible surgical flashlights. If such tools are held by the surgeon, however, they tie up a hand that the surgeon may need for other manipulations. If such tools are held by other members of the surgical team, the person holding the light may not be able to direct it accurately towards what the surgeon wants to have illuminated. To overcome some of the limitations of the aforesaid lighting systems, surgeons may elect to wear conventional surgical headlights. These devices, however, have limitations as well. Surgical headlights commonly are heavy, uncomfortable and hot. The light may require periodic or and possibly frequent redirection so that it is properly aimed along the line of the surgeon's sight. Other members of the operating team may need to exercise caution so that they do not block or strike the surgeon's light, especially when procedures are being undertaken in deep body cavities. The light itself may generate sufficient heat that it can burn tissues if it comes in contact with them. Furthermore, the headlight and all related apparatus is unsterile, so the surgeon and the operating team must be cautious so as to avoid contamination of the surgical field. A need therefore remains in the art to provide an easy to use lighting system that may be directed specifically at a surgical site or other workpiece being manipulated. There is a further need in the art for such a system adapted for single use disposability. Advantageously, such a system would avoid interference with the actual performance of the operation, including the motions and maneuvers carried out by the entire surgical team to carry out the surgery safely.

Other settings will be evident to those of ordinary skill in related arts where a lighting accessory directable to a recessed area or other inaccessible region would be useful. In particular, there is a need for a tool that can illuminate an object to be grasped in a difficult to reach area and that will not obstruct the grasping of the object.

SUMMARY

In one aspect, the present invention provides a lighting accessory system that comprises an anchoring base affixable to a proximal end of the tool, a lightguide using a fiber-optic fiber whose proximal end is attached to the anchoring base and whose distal end extends distally along a face of the tool to illuminate a distal surface of the tool, and a fiber-optic cable assembly connected to the proximal end of the fiber-optic fiber that conveys light energy thereto. The lighting accessory system may also include an attachment clip that attaches the lightguide to the face of the tool. In certain embodiments, the anchoring base may cover the proximal end of the tool. In certain embodiments, the lightguide may comprise a hypotube. The hypotube may be adjustable. The lightguide may be centered on the tool. In certain embodiments, the anchoring base may include an attachment means. In some embodiments, the attachment means may be selected from a group consisting of friction fit, set screws, ratchets, cable ties, adhesives, spring clams, roller clamps, cam or lever locks, elastic material or hook and loop fasteners, welding, rivets, tight friction fit, or chemical bonding. The attachment means may comprise an elastomeric polymer. In certain embodiments, the tool may comprise two arms that converge proximally to attach to each other with the face of the tool located on an outer surface, or an inner surface, or a top surface, or a bottom surface of an arm. The tool may be a forceps selected from the group consisting of Adson forceps, DeBakey forceps, neuro forceps, bayonet forceps, jewelers forceps, smooth pickups, and toothed pickups. In certain embodiments, the lighting accessory system may further comprise a light adapter for attaching a light pipe on the fiber-optic cable to a light source, the light adapter comprising a body having a lumen, a proximal end for connection to a light source, and a distal end for connection to a fiber-optic cable, and also having a light transmitting insulator positioned in the proximal end, and further having a means for anchoring the fiber-optic cable. In certain embodiments, the light transmitting insulator is glass. In certain embodiments, the means for anchoring the fiber-optic cable comprises at least one of the following: an iris, set screws, ratchets, adhesives, spring clamps, trumpet valve clamps, roller clamps, cam or lever locks. In certain embodiments, the iris may be an elastomeric iris. In certain embodiments, the light adapter may further comprise a heat sink. In certain embodiments, the light adapter may further comprise a visual indicator to indicate insertion of the light pipe. In certain embodiments, the light adapter may be molded or bonded to the fiber-optic cable.

In another aspect, the present invention provides an illuminable tool, having a forceps with a first arm and a second arm that converge proximally to join a proximal end of the forceps, with the first arm extending distally to terminate in a first grasping tip, and the second arm extending distally to terminate in a second grasping tip, and also having a fiber-optic fiber removably affixed to at least one arm of the forceps, and having a proximal end attachable to a light source and a distal end positionable at a distal part of the at least one arm, wherein the fiber-optic fiber transmits light that nonobstructingly illuminates an object adjacent to and graspable between the first grasping tip in the second grasping tip. By nonobstructingly illuminating the object, the fiber-optic fiber does not mechanically impair the grasping of the object by the grasping tips. In certain embodiments, the illuminable tool may comprise a surgical forceps. The surgical forceps may be selected from the group consisting of Adson forceps, DeBakey forceps, neuro forceps, bayonet forceps, jewelers forceps, smooth pickups, and toothed pickups. The fiber-optic fiber may be affixed to an inner face, an outer face, a top face, or a bottom face of the at least one arm. The fiber-optic fiber may be carried within a lightguide assembly. In certain embodiments, the illuminable tool may further comprise an anchoring base that attaches the fiber-optic fiber to the proximal end of the forceps. The anchoring base may cover the proximal end of the forceps. The anchoring base may be removably attach to the forceps. The illuminable tool may further comprise a light cable removably attached to the proximal end of the fiber-optic fiber. The light cable may include a fiber-optic cable assembly. In certain embodiments, the illuminable tool may further comprise an anchoring clip that affixes the fiber-optic fiber to the forceps distal to the proximal end of the forceps and proximal to the grasping tip of the at least one arm. The fiber-optic fiber may be partially embedded in the at least one arm, or it may be positioned within a group in the at least one arm. In certain embodiments, the fiber-optic fiber is completely embedded within the at least one arm.

In another aspect, the present invention provides an illuminable tool adapted for manual use, having a forceps with two arms converging proximally to join at a proximal end and extending distally to terminate in grasping tips, at least one of the two arms including a fiber-optic illuminating means to illuminate a workpiece adjacent to and graspable by the grasping tips, the fiber-optic illuminating means being dimensionally adapted for permitting the approximation of the grasping tips without obstruction thereof. In certain embodiments, the forceps may be surgical forceps.

BRIEF DESCRIPTION OF THE FIGURES

The following figures depict certain illustrative embodiments of the invention in which like reference numerals refer to like elements. These depicted embodiments are to be understood as illustrative of the invention and not limiting in any way.

DESCRIPTION OF THE INVENTION

Certain principles of the present invention will be illustrated by a description of embodiments particularly useful in the field of medicine. It is recognized, however, that these principles are readily applicable to other fields of use, as will be appreciated by skilled artisans in the relevant disciplines.

FIG. 1-A shows an embodiment of a lighted forceps system 10 according to the present invention. In the illustrated embodiment, a forceps 20 is shown that may be adapted for use in a setting such as surgery, to which is attached a lighting system. The lighting system includes an anchoring base 12, a lightguide 14, and a fiber optic cable assembly 18. In the depicted embodiment, the lightguide 14 passes through an aperture 22 in the anchoring base 12. The lightguide 14 may be formed of a hypo tube or of any other suitable material through which may pass the distal end of the fiber optic cable assembly 18. The lightguide 14 may hold the distal end of the fiber optic cable assembly 18 parallel to the shank of the forceps in a rigid fashion. In one embodiment, the distalmost end of the fiber optic cable assembly 18 may protrude from the lightguide 14, or the fiber optic fiber may end flush with the distal end of the lightguide 14. It is envisioned that the lightguide 14 may be combined with prisms, lenses or other optical instrumentation that might permit focusing, redirection, amplification or other modification of the light beam, as will be appreciated by practitioners of ordinary skill in the art In the depicted embodiment, the anchoring base 12 of the lighting system is formed to slide over the proximal end of the forceps 20. Advantageously, the anchoring base 12 may be fabricated from an elastomeric or rigid material so that it can slide onto the proximal end of the forceps 20 with finger pressure, and so it further will be retained thereon. Various elastomeric materials may be used to form the anchoring base 12, as will be understood by practitioners in the relevant arts. In certain embodiments, the present invention may be suited for single use as a disposable product. In other embodiments, the present invention may be formed of materials permitting resterilization for multiple use, and some or all of the components may be so adapted. Certain embodiments of the invention, as depicted in this and other figures of the present disclosure, may be provided to the user in large, multi-device packs usable in open or in laparoscopic surgical procedures, and certain embodiments may contain all or some of the components of the present invention provided disposably or reusably. The lighting system of the present invention may also be combined with radio-opaque markers so that an inadvertently dislodged device could be detected within a body cavity.

Figure 8A:
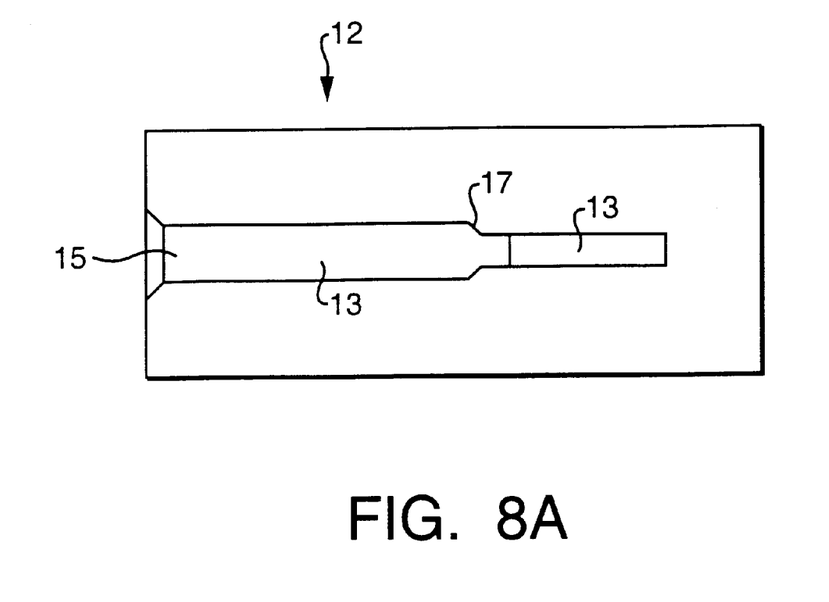
FIG. 8A shows a schematic cross-sectional top view of a portion of the anchor base.
Figure 8B:
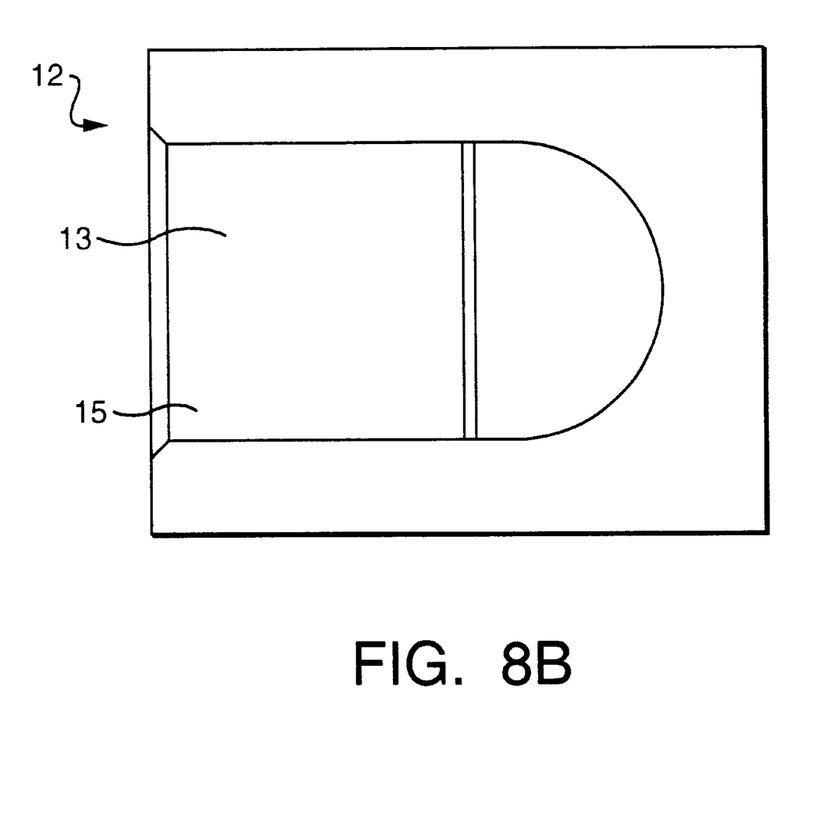
FIG. 8B shows a schematic cross-sectional side view of a portion of the anchor base.

The dimensions of the anchoring base 12 can be varied depending on the size of the tool and the elastomer used. A preferred embodiment of the base which will fit the majority of forceps used in surgery may be manufactured out of 55A durometer Dynaflex G792755 elastomer. Certain of its features are illustrated in FIGS. 8A and 8B. Dynaflex®G792755, containing Krayton®, is a product available from GLS Plastics of 833 Ridgeview Drive, McHenry, Ill. 60050. As shown in FIG. 8A, the anchor base 12 has a central slot 13 having a uniform height of about 0.500 inches and a width that varies from about 0.090 at the opening 15 of the slot 13 to a narrower width of about 0.050 inches at a preselected position 17, here shown to be about halfway in the slot. The wider opening 15 in the slot provides an adequate interference fit for larger forceps, and the narrower dimension of the slot 13 at the preselected position 17 provides an adequate interference fit for smaller or thinner forceps. The slot 13 may be optionally radiused or chamfered or modified in other ways to facilitate fixation of the forceps, entry of the forceps into the slot 13 or removal therefrom, as will be appreciated by ordinarily skilled artisans. The depicted embodiment advantageously maximizes the range of forceps that can securely fit in the slot 13. In the depicted embodiment, forceps with a width from about 0.137 to about 0.075 inches may fit securely in the slot 13 because of the tight friction fit involved. While the depicted embodiment shows, in FIG. 8B, a slot 13 with a height of about 0.500 inches, the precise height of the anchoring base 12 and its slot 13 may be varied without consequence, since the forceps (not shown) is stabilized in the anchoring base 12 by the friction generated along its sides as they contact the lateral walls of the slot 13. Since a majority of commercially available forceps usable with this product have height dimensions less than 0.500 inches, with a range of 0.393 to 0.480 inches being known in the art, an exemplary height for the slot 13 of 0.500 inches may be used.

Alternative embodiments of the present invention are illustrated in FIGS. 1-B, 1-C, and 1-D. As shown in FIG. 1-B, an anchoring base 12 may be used on the proximal end of the forceps 20 with a distal clip 24 being placed on one of the legs 30 of the forceps 20. In this embodiment, a fiber optic fiber (not shown) that forms a part of a fiber optic cable assembly (not shown) may be affixed to the anchoring base 12 proximally and then run distally along a top, medial or outer surface of the forceps leg 30 to be held by the distal clip 24, whereby its illumination is directed to the workpiece being manipulated by the forceps 20. The embodiment depicted in FIG. 1-C shows a variation of this arrangement wherein the proximal anchor 32 does not cover the entire proximal end of the forceps 20. This mini-base 32 may be combined with a distal clip 24 to provide support for a fiber optic fiber (not shown) that may be directed to illuminate a workpiece being manipulated by the forceps. The mini-base 32, like the anchoring base previously described, may be made of an elastomeric material or of any suitable material conformable to the proximal end of the forceps 20 and permitting the attachment of the fiber optic fiber. The embodiment shown in FIG. 1-D shows an anchoring base 12 as previously described mounted on the proximal end of a forceps 20. In this embodiment, two distal clips 24 are shown, one on each leg 30 of the forceps 20. This arrangement may permit two monofilament fiber optic fibers (not shown) to be secured along the forceps legs 30, each one being attached proximally to the anchoring base 12 and being attached distally to its respective distal clip 24.

Figure 1A:
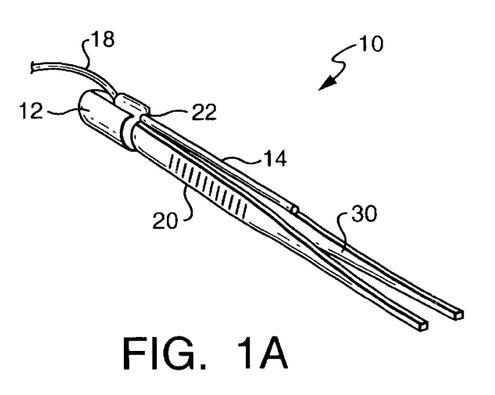
FIGS. 1A–D are perspective views of embodiments of lighting accessory system according to the present invention.
Figure 1B:
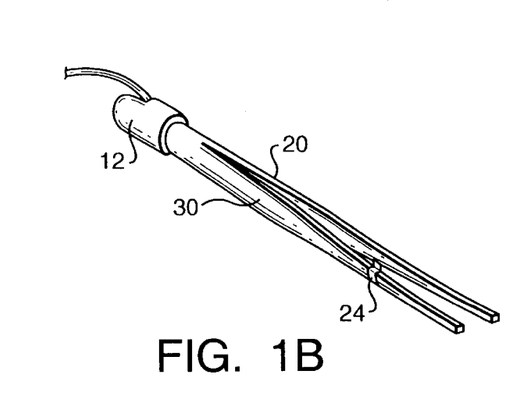
Figure 1C:
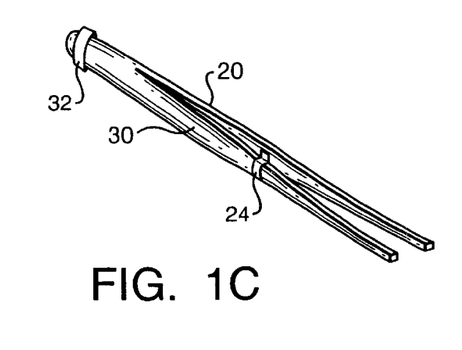
Figure 1D:
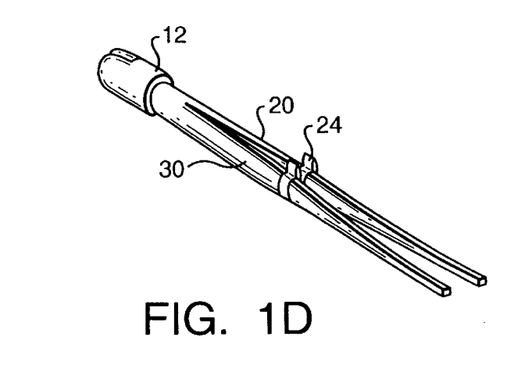
Figure 2:
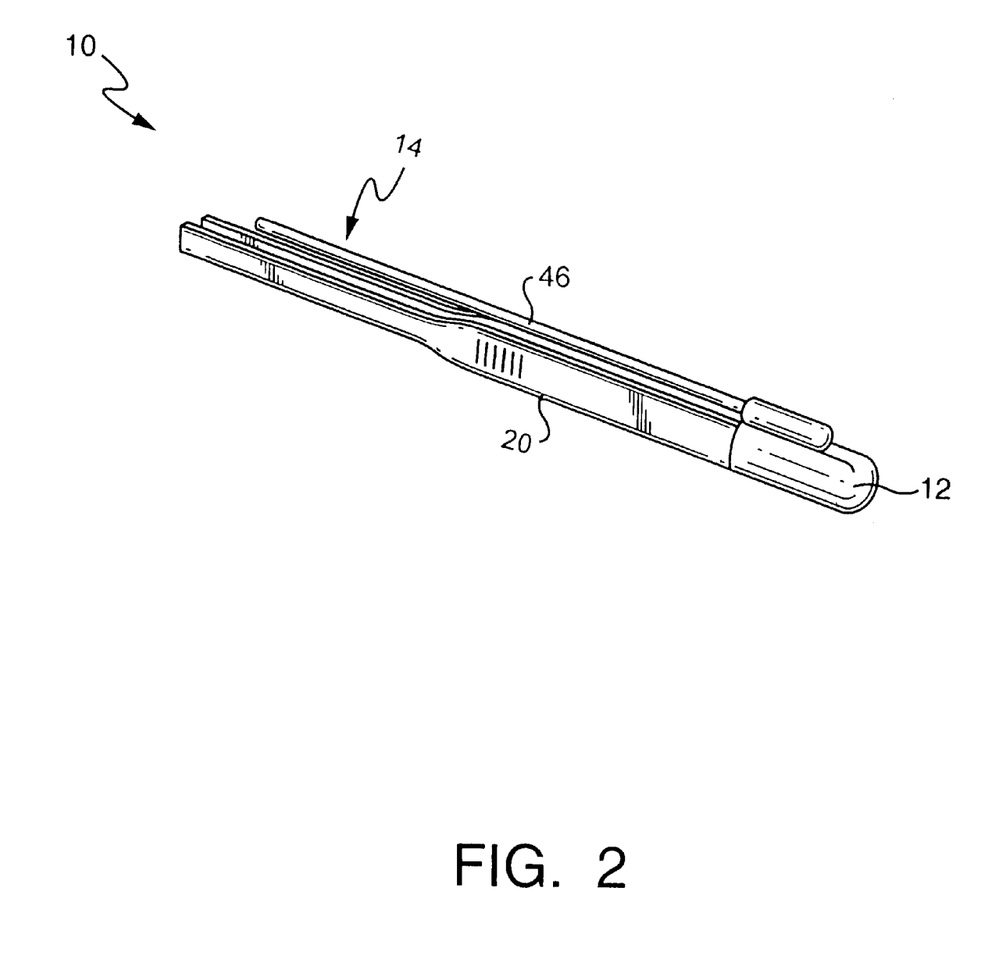
FIG. 2 provides a perspective view of a lighting accessory system according to the present invention.

FIG. 2 shows in more detail a forceps 20 to which has been affixed an anchoring base 12. In the depicted embodiment, a lightguide 14 has been inserted firmly into the anchoring base 12 to fix it therein. This figure illustrates a rigid lightguide 14 formed of a hypotube 46 through which passes a fiber optic fiber (not shown). While the depicted embodiment illustrates one type of forceps 20, it is understood that the present invention is adaptable to any type of forceps or to other tools. As will be understood by skilled practitioners, the present invention may not be confined to a medical setting, but may be used to provide illumination as an accessory to a variety of grasping tools and other tools. Further, as will be understood by skilled artisans, the present invention may be combined with other accessories affixable to surgical, medical, or other instruments. For example, the present invention may be combined with devices for cauterizing or coagulating tissues, or other devices of suitable dimension to be attached to surgical, medical or other hand tools. Advantageously, the present invention may provide illumination using a device that is less bulky than retractors containing fiberoptic bundles.

Figure 3A:
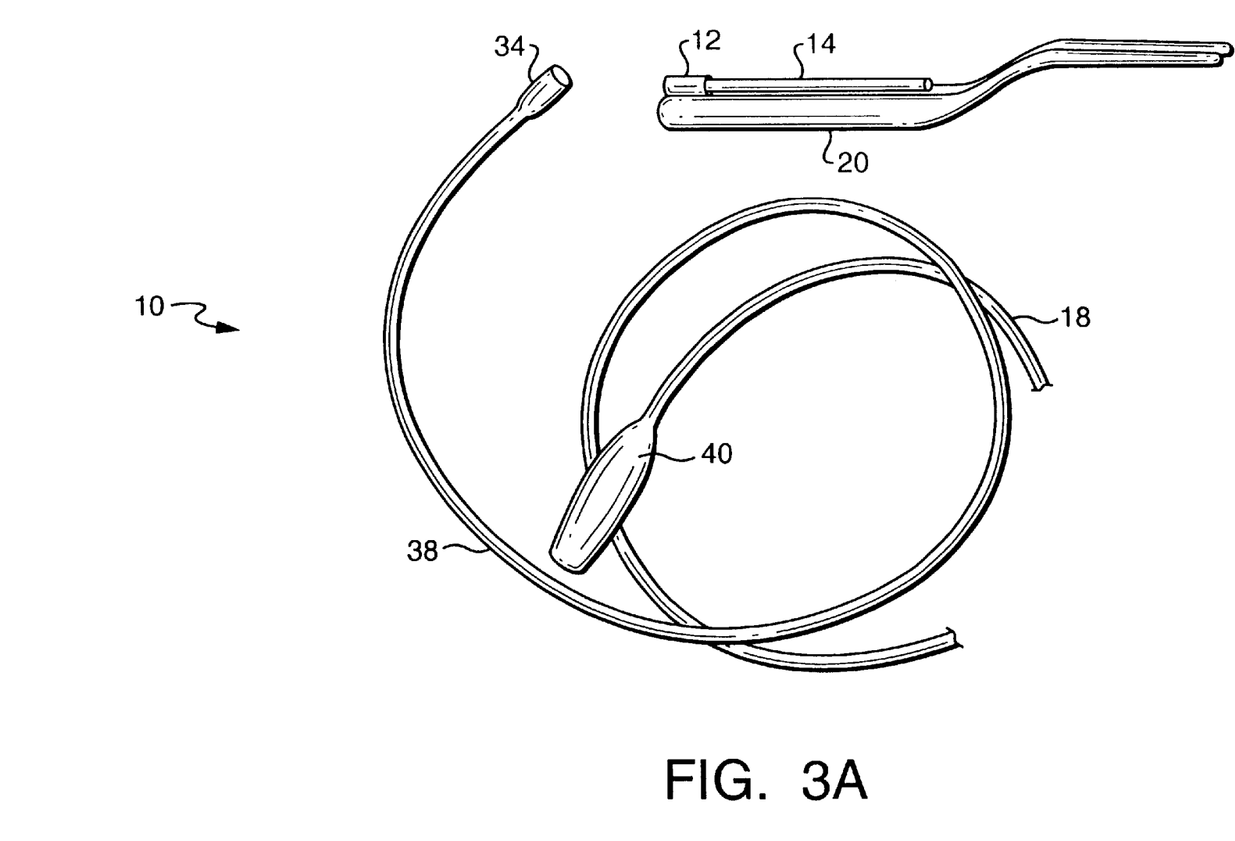
FIGS. 3A–B show embodiments of a lighting accessory system including a fiberoptic cable assembly.
Figure 4A:
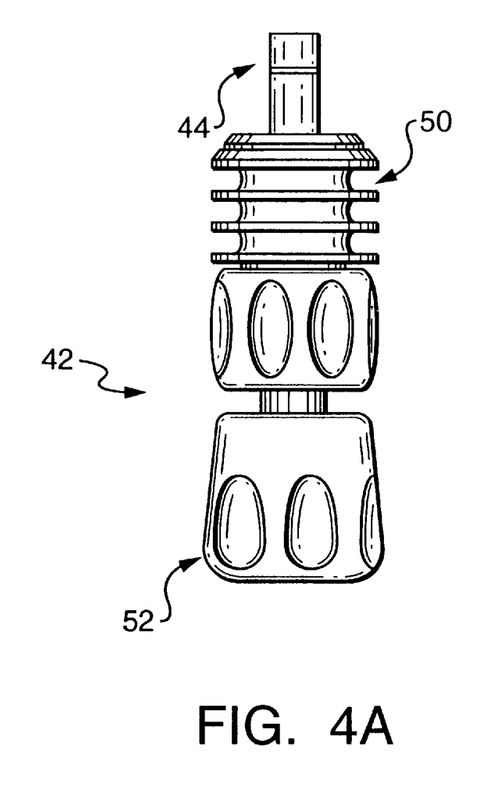
FIGS. 4A–B show a side view and a cross-section of a light source adapter according to the present invention.
Figure 4B:
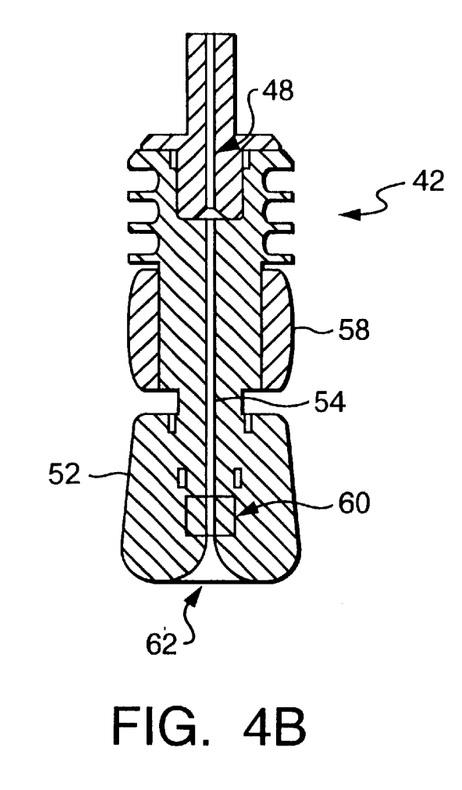

FIG. 3A shows in more detail one embodiment of a lighting accessory system 10 according to the present invention. A forceps 20 is shown, having an anchoring base 12 mounted on its proximal end. Affixed to the anchoring base 12 is a lightguide 14 which conveys illumination from a fiber optic cable assembly 18. The fiber optic cable assembly 18, as depicted in this Figure, includes a distal connector 34 suitable for attaching to the proximal end of the lightguide 14. Advantageously, this distal connector 34 may be made from a lightweight material so that it does not interfere with the handling of the forceps 20 by the operator. The stiffness of the hypotube lightguide 14 may allow the light bearing element of the lighting system to be self-supporting so that it does not interfere with the operator's fingers or hand. The length of the hypotube guide can be lengthened or shortened by moving the hypotube within the anchor base. As depicted herein, manipulation of the forceps 20 and its legs are not affected by the position of the lighted forceps system 10 on the proximal end of the forceps 20. Advantageously also, this distal connector 34 may decrease the transmission of heat so that the handheld forceps 20 and its attached distal connector 34 will remain cool in the operator's hand. The fiber optic cable assembly includes a light pipe 38 that can carry illumination with minimal loss thereof from a light source (not shown) to the lightguide 14. While any suitable fiber optic material may be used, either as monofilaments or as multi-fiber bundles, the use of plastic components, including polymethylmethacrylate monofilament fiber optic, may allow low-cost manufacturing for a disposable product. A small profile, low-weight light pipe according to the present invention can be attached to a variety of tools that have a variety of sizes and shapes. A connector 40 is provided at the proximal end of the fiber optic cable assembly 18, permitting its attachment to a conventional light source (not shown). In one embodiment, this connector may be formed as a boss adapter for a light source, described in more detail in FIGS. 4-A and 4-B, shown here attached to the proximal end of the fiber optic cable assembly 18.

Figure 3B:
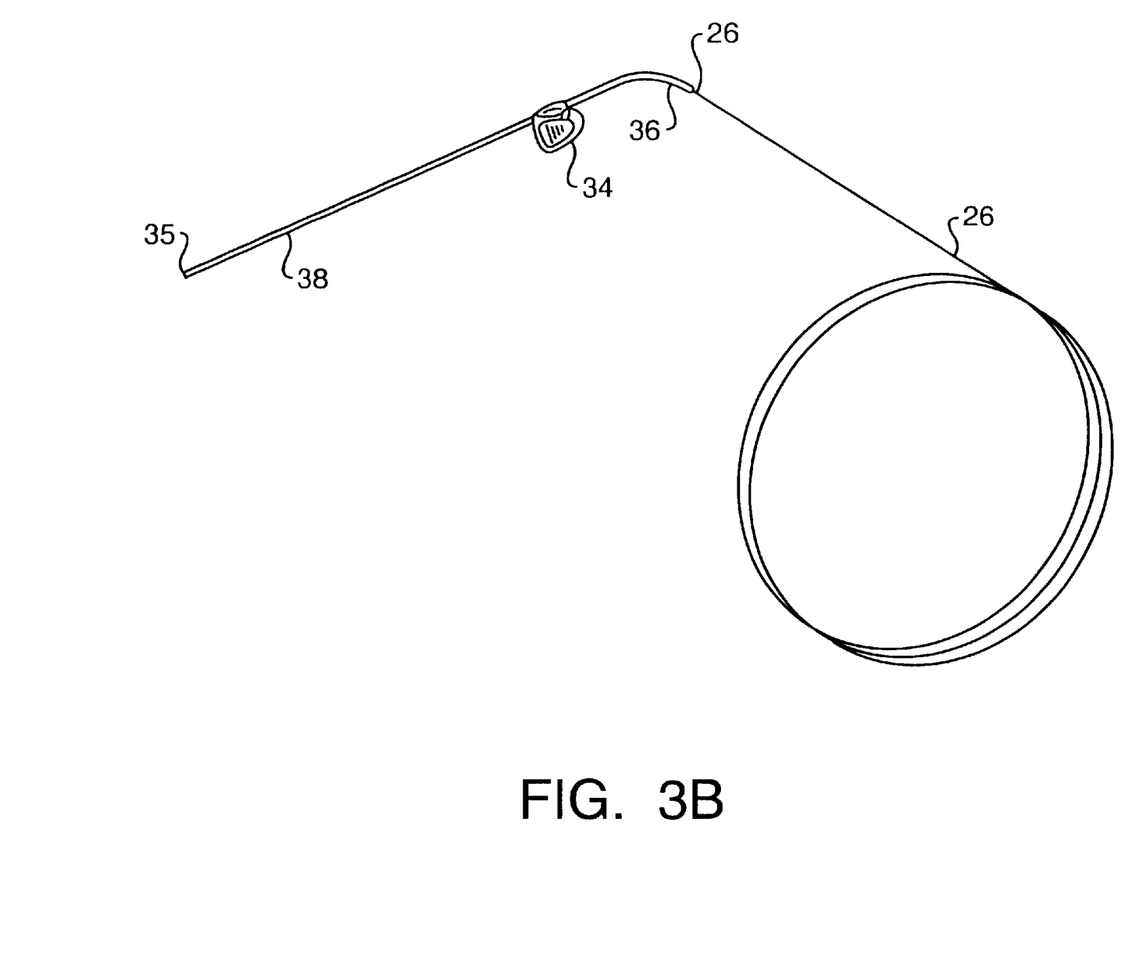

FIG. 3B shows an alternative embodiment of a lighting accessory according to the present invention. The system depicted in this figure is adapted for attachment to a forceps or other hand tool (not shown). The figure shows a light pipe 38 having a proximal end 36 and a distal end 35, through which may pass an optical fiber 26. The optical fiber 26 may be a monofilament optical fiber of small caliber, for example 1.5 mm, and may extend proximally to extend through the forceps mounting clip 34 that is adapted for connecting the lighting accessory to the distal end of a forceps or other hand tool (not shown). The optical fiber 26 may further extend proximally to couple with a light source (not shown) that provides light energy to be conducted through the optical fiber 26 to illuminate the workpiece being manipulated by the forceps or other hand tool (not shown). In the depicted embodiment, light energy may pass through the optical fiber 26 to be emitted distally at the distal end 35 of the light pipe 38. In the depicted embodiment, a length of heat shrink tubing 26 is available to conduct the optical fiber 26 into the light pipe 38.

FIGS. 4-A and 4-B illustrate a light source adapter 42 suitable for use with the present invention. This light source adapter 42 may act as a connector to permit the passage of light from a light source into the light pipe of the fiberoptic cable assembly described above. FIG. 4-A shows a side view of the light source adapter 42. An interface 44 is shown that is connectable to the aforesaid light source (not shown). The interface 44 may be changed to provide compatibility with different models of light sources. As shown in the cross-sectional view in FIG. 4-B, the interface 44 contains within it a glass rod 48 that permits the transmission of light from the light source into the adapter. Advantageously, a heat sink 50 may be provided proximally on the light source adapter 42. Distally on the light source adapter 42, a handle 52 is provided into which may be inserted the proximal end of the light pipe (not shown). As shown in the cross-sectional view, a passage 54 passes through the handle into the body 58 of the light source adapter 42. Light entering the light source adapter 42 from a light source (not shown) passes through the glass rod 48 into the passage 54 thereby to enter the light pipe (not shown). A clamping means is provided within the handle of the light source adapter to hold the light pipe in the adapter. The clamping means can be any suitable means for holding the light pipe in the adapter. A preferred embodiment comprises an iris or most preferably an elastomeric iris 60. The elastomeric iris 60 is provided within the handle 52 of the light source adapter 42. The elastomeric iris 60 loosens and tightens as the handle is rotated appropriately. The elastomeric iris 60 is opened to permit insertion of the light pipe (not shown); the light pipe is then secured in position by closing the elastomeric iris 60. A funnel 62 may be provided to facilitate insertion of the light pipe (not shown) into the adapter 42. The depicted adaptor may allow a monofilament or jacketed fiberoptic cable to be connected to a standard light source without special metal adaptors on the light pipe. Advantageously, this feature may be fabricated from low-cost disposable materials to permit its usage with a low-cost disposable lightpipe.

Alternate means of fixating the fiber in the adapter body will be apparent to those of ordinary skill in the art. Such fixation means may include locking features formed or affixed on the fiber optic itself. These features may be fabricated from polymers, elastomers, metals, and the like, and may be affixed with adhesive or through an interference fit. In an exemplary embodiment of a fixation system, the adapter body may have some mating features which when engaged with the fiber optic features retain the fiber optic with some force maintaining optimal spacing between the fiber end and the glass rod. The fixation system may then interact with the fiber to hold it in place so that it could not be inadvertently displaced from the adapter. In those embodiments wherein it becomes necessary to remove the fiber from the adapter, the fixation system may be arranged so that pulling the fiber with enough force overcomes the fixation thereof. Alternatively, a release mechanism may be provided whereby the user could disengage the fixation. In certain embodiments, the fixation system may be adapted for locking a bare fiber in position, where the bare fiber lacks any complementary features to facilitate its fixation. In these embodiments, an adapter actuated by the user may permit either the grasping or the release of the fiber. Such an adapter may include a spring loaded piece which forces the fiber against an internal adapter surface, providing a certain level of frictional resistance to fiber removal. In this case the user deforms the spring to remove the force from the fiber and release it. Alternatively, such an adapter may employ a sliding piece which when moved into one position cams into an interference with the fiber while at the same time forcing it towards the glass rod. Moving the sliding piece in the opposite direction cams the piece away from the fiber, removing any retention force. Other mechanisms for providing a removable fixation force to a member will be apparent to skilled artisans in the field.

Figure 5A:
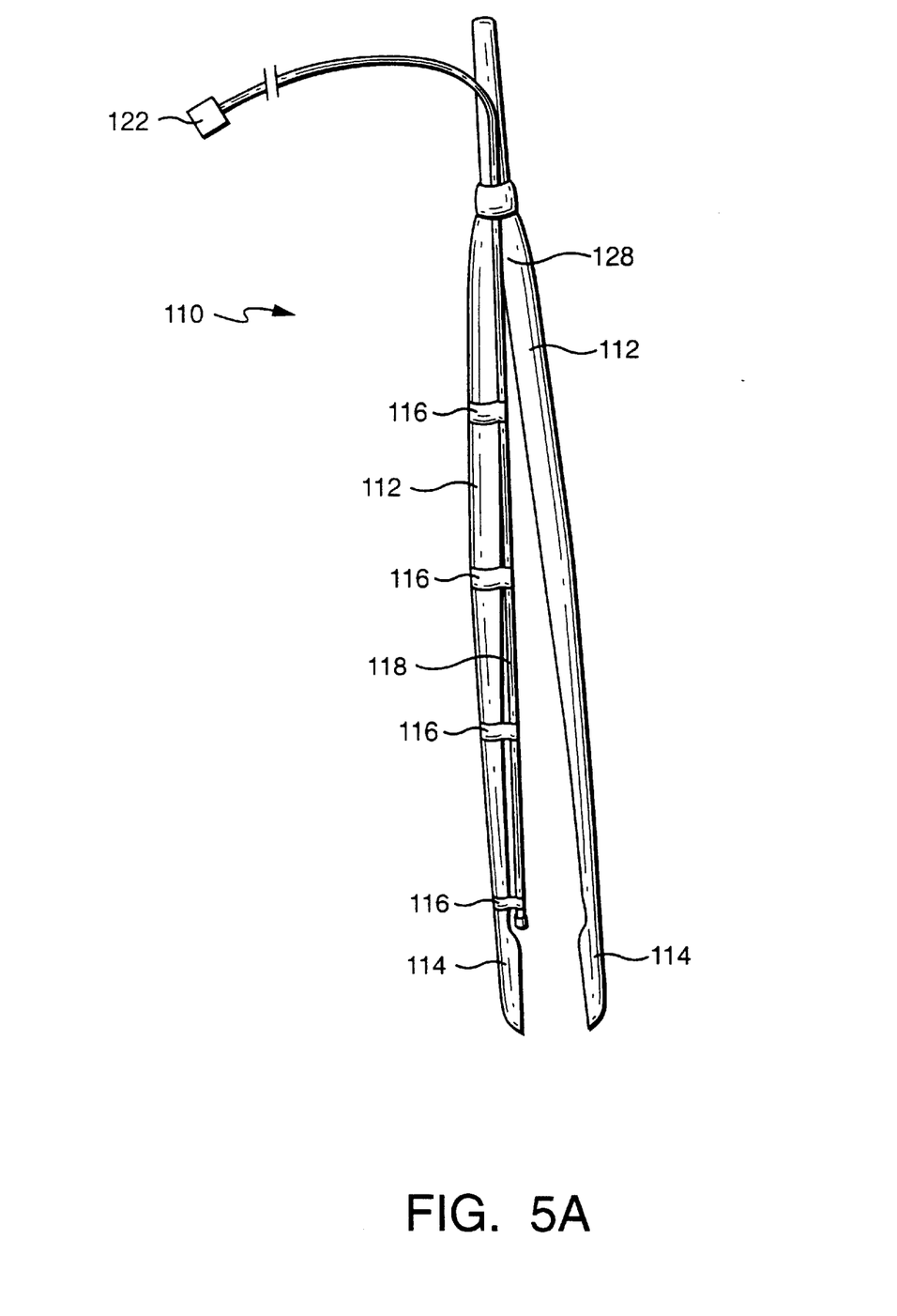
FIGS. 5A–B show an embodiment of a lighting accessory according to the present invention.

FIG. 5A depicts one embodiment of the present invention wherein a familiar type of surgical forceps have been retrofitted with an illumination mechanism. The depicted embodiment shows a pair of surgical forceps 110 fabricated in the standard manner, having two arms 112, each with a distal grasping tip 114 and each joined to the other proximally at an elbow 128. The present invention may be applied to any type of forceps familiar in the surgical arts or used in nonsurgical fields. For example, the present invention may be applied to jewelers forceps, toothed or non-toothed Adson forceps, DeBakey forceps or any other forceps familiar to surgical practitioners. The grasping tip 114 may be smooth or toothed, or provided with any of the conventional surfaces or conformational modifications familiar to skilled artisans. In the embodiment depicted in FIG. 5A, a single fiber of fiberoptic light pipe 118 may be carried from the proximal portion of the forceps, past the elbow 128 and down one or both arms 112 to a point proximal to the grasping tip 114. In arranging the fiberoptic light 118 on the arm or arms 112 of the forceps 110, it is important that the light 118 itself does not impinge upon the grasping surfaces of the grasping tip 114. To accomplish this, the fiberoptic light 118 may be positioned at the distal aspect of the forceps on one of the external surfaces, although more proximally it may be desirable to have the fiberoptic light 118 affixed to the inner surface of the arm 112 so that it does not interfere with the area where the surgeon holds the forceps. The embodiment depicted in this figure presents another arrangement, wherein the fiberoptic light 118 is held on the inner surface of the arm 112 down to the grasping tip 114, being secured just proximal thereto. In this figure, a set of restraining clips 116 is shown holding the fiberoptic light 118 in place on the arm 112. Other types of restrainers may be used, whether metal or plastic, to secure the fiberoptic fiber 118 in place. Preferably, the affixation means permits the fiber 118 to be removed from the forceps 110 at the conclusion of the procedure. The restraining clips 116 may be disposable for single use or may be reusable and sterilizable. The restraining clips 116 are fabricated and positioned so as not to interfere with the sterilizability of the forceps 110.

Figure 5B:
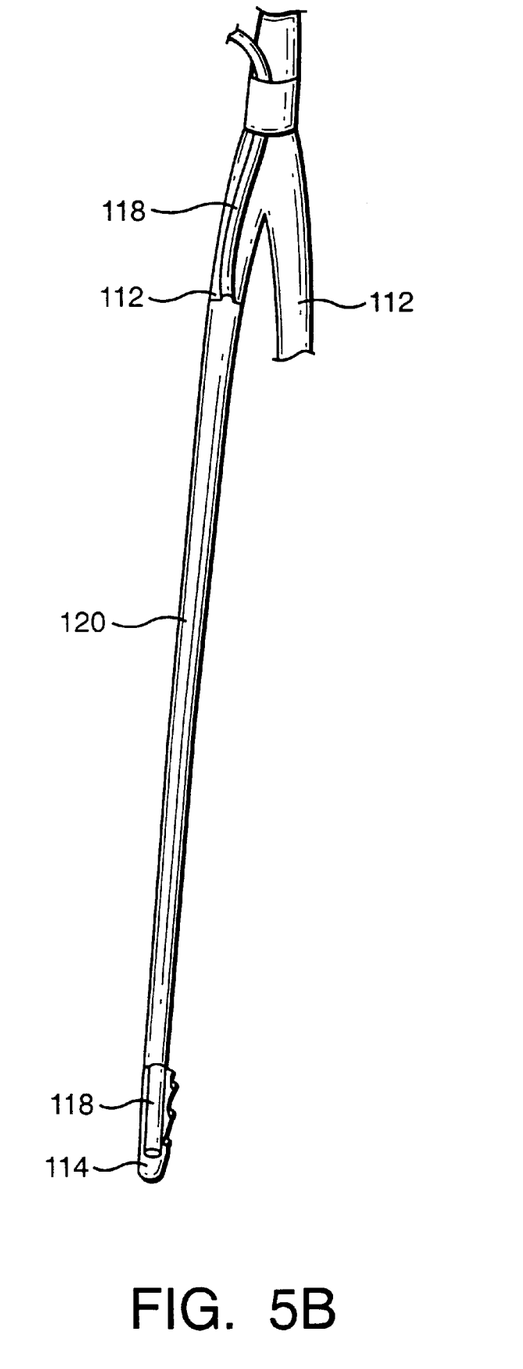

Alternatively, the fiberoptic light 118 may be held in place on one or both arms 112 by a Teflon sheath 120 that sterile affixes the sterile fiberoptic light 118 to the arm 112, as shown in FIG. 5B. FIG. 5B shows a fiberoptic light 118 held by a Teflon sheath 120 on the top portion of an arm 112, in a position where it does not impinge upon the grasping tip 114.

As shown here, the fiberoptic light 118 is positioned on the top of the arm 112, although any position is acceptable, so long as the fiberoptic light 118 does not interfere with the closure of the grasping tips 114. As shown in FIG. 5A, the fiberoptic light 118 is connected more proximally yet to a connector 122 that permits its attachment to the appropriate light source (not shown). In one embodiment, a fine filament fiberoptic light may be used, similar to that provided by Grieshaber for use in vitreous surgery. While this particular product is commercially available, it is understood that any similar fiberoptic filament (preferably a monofilament) could be used as long as its weight and handling characteristics do not impede the normal use of the surgical forceps. The fiberoptic filament advantageously would be constructed to permit total internal reflection, so that the maximum amount of transmitted light is emitted at the tip.

Figure 6A:
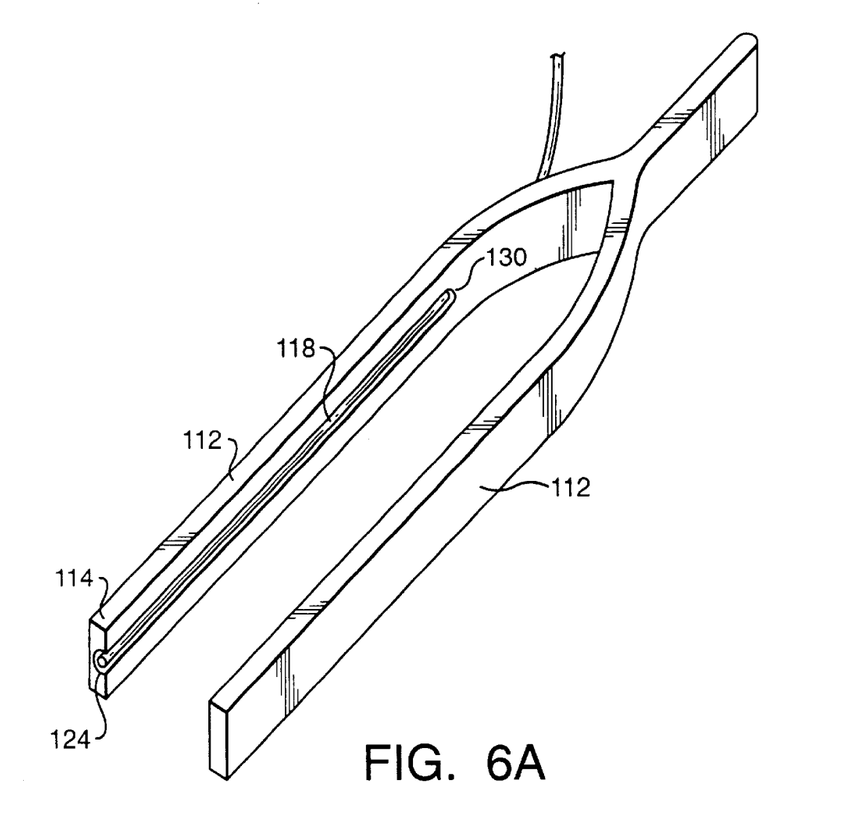
FIGS. 6A–C show perspective and end-on detail views of an embodiment of a lighting accessory according to the present invention.
Figure 6B:
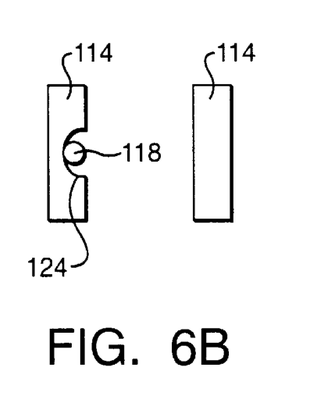
Figure 6C:
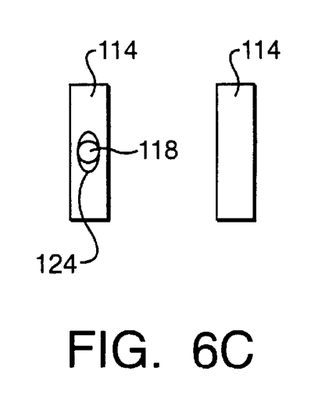

FIG. 6A depicts an embodiment of a forceps according to the present invention specifically constructed to incorporate an illuminating element. In the depicted embodiment, the fiberoptic fiber 118 is imbedded in a specially constructed groove 124 in one arm 112 or in both arms. The fiberoptic fiber 118 may run distally in its groove into the grasping tip 114 so long as it is sufficiently imbedded in the groove that it does not impinge upon the grasping function of the grasping tip 114. In the depicted embodiment, a channel 130 has been bored through the proximal arm 112 or the elbow 128 so that the fiberoptic fiber 118 may exit the forceps and interface with its connector (not shown). In one embodiment, the groove 124 may extend through the entire grasping tip 114 as a channel down the middle of the grasping tip 114 that has grasping surfaces on either side, as shown in the end-on view provided in FIG. 6B. Other arrangements may be envisioned by practitioners in these arts whereby the grasping function of the grasping tip 114 would not be affected by the fiberoptic fiber 118 in its groove. FIG. 6C shows, as an example, the end-on view of a distal tip 114 wherein the groove 124 is entirely within enclosed the distal tip 114, so that the tip material covers the fiberoptic fiber 118 completely. Embodiments of the present invention may also be envisioned wherein several grooves 124 may be formed along the inner aspect of an arm 112 of a surgical forceps, with each groove permitting a fiberoptic fiber 118 to be sufficiently recessed that it does not impinge upon the grasping tip 114 of the device. In such embodiments, channels may be bored through the proximal arm 112 or the elbow 128 of the forceps through which the fiberoptic fibers 118 may pass heading proximally toward a connector.

Figure 7:
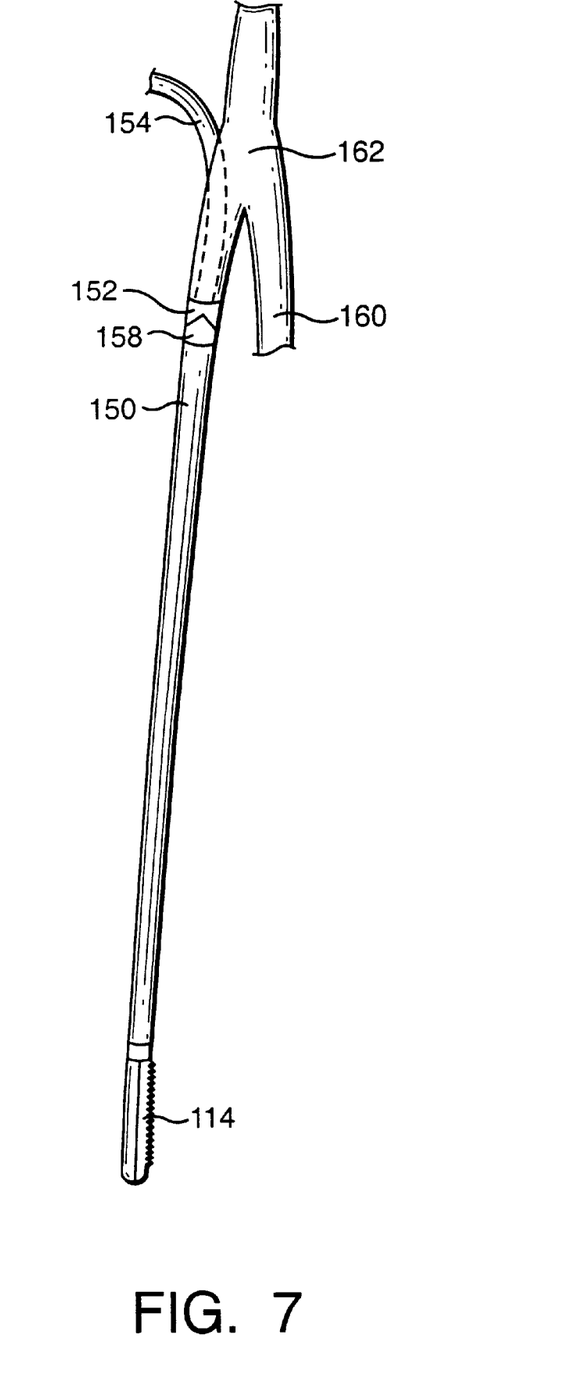
FIG. 7 shows a partial perspective view of a lighting accessory system according to the present invention.

FIG. 7 shows an embodiment of an illuminated forceps with one conventional arm 160 made from standard materials such as titanium, stainless-steel, ceramics or plastics, and the other arm 150 being made from a material that can act as a fiberoptic light guide. Preferably, the fiberoptic arm 150 has surface characteristics that permit total internal reflection down to the distal most part that comprises the grasping tip 114. At that level, the surface of the fiberoptic arm 150 may be treated so that light may be emitted in a preselected area. The elbow 162 of the device allows the two arms to meet, as in a standard surgical forceps, and additionally permits the interface of the forceps with a light cord 154 that brings in light from a standard light source. In one embodiment, the light cord 154 interfaces with a fiberoptic connector 152 and a light guide 158 that transmits illumination to the fiberoptic arm 150. All these elements may be fabricated from lightweight materials that do not interfere with normal surgical handling of the device.

It will be understood that the embodiments described above are illustrative of some of the applications and principles of the present invention. Various modifications may be made by those skilled in the art without departing from the spirit and scope of the invention. For example, different materials and shapes can be employed for forming the different elements of the lighting system. As another example, additional distal clips could be used to attach the lightguide to the leg or legs of the forceps closer to the forceps tip. Alternatively, it is possible to design a continuous one piece clip that attaches to a leg of the forceps. The light guide could surface mounted or could be incorporated into the body of the clip. Or, for example, the anchor base could be made in a variety of different geometries and configurations to permit proper fixation of the anchor base to differently sized or shaped forceps. Alternative configurations could include single piece or multi-piece anchor bases. Multi-piece bases could include the use of a separate outer shell that mounts over an inner shell in which the outer shell would work in connection with the inner shell to hold the lightguide onto the instrument. Such outer shell could take the form of a cap, with or without pinch points, a sliding sleeve, or wedge shapes. Optionally, the inner shell would be of a softer material than the outer shell. Such alternative anchor base configurations, in addition to friction fit, could further include one or more locking mechanisms for mounting the base to the forceps, such as: set screws, ratchets, cable ties, adhesives, spring clamps, roller clamps, cam or lever locks, elastic bands or hook and loop fasteners. In addition, the anchor base could permit the lightguide to be attached thereto through a variety of mechanisms, including mechanisms that provide a snap on connection such as compressible polymer foam, set screws, elastically deformed prongs to provide friction, and a range of latches, clasps, clamps and other affixation mechanisms familiar to those of ordinary skill in the art. Devices desiring permanent attachment of the base or lightguide could utilize welding, rivets, tight friction fit or chemical bonding as a means of attachment the base and/or lightguide to the tool.

Furthermore, the lightguide as used in the present invention may be either rigid or flexible. A flexible lightguide may be formed, for example, from a pliable polymer tube that has a metal wire inside. In such an embodiment, the polymer light tube may be manipulated into a particular geometric configuration to focus the light properly on the target. The result of this manipulation would then be firmly retained by the metal wire.

The fiber optic cable assembly as used herein may of any suitable thickness or material including but not limited to glass or acrylics. Most preferred is a 1.5 mm acrylic material.

The light source adapter may further be designed to duplex a light source to allow its use by multiple instruments. Such light source adapter may be designed to interface with any suitable light source or other fiber optic cables. This includes fiber optic bundles currently in use in many hospital settings or attaching to other devices. The adapter could include a visual indicator, such as a pop up or pop out device, for confirming the fiber optic cable is properly inserted into the adapter. Optionally, a rotating adapter can be included on the light source adapter and/or the light tube to reduce torque transmitted to the user by the twisting fiber optic cable. The light source adapter may further use one or more other clamping means instead of an iris for holding the light guide such as: set screws, ratchets, adhesives, spring clamps, trumpet valve clamps; roller clamps, cam or lever locks.

The embodiments depicted and described provide illustrations of adjustable or flexible light sources according to the present invention. Other embodiments demonstrating this principle and other principles of the present invention may also be produced using no more than routine experimentation. Other modifications, substitutions and additions can be also made without departing from the scope of the invention. Accordingly, the invention is not to be limited to the illustrated embodiments provided above, but is to be understood by the claims set forth below, which are to be interpreted as broadly as allowed by law.

What is claimed is:

1. An illuminable tool, comprising:
   a forceps having a first arm including a proximal end and a distal end and a second arm including a proximal end and a distal end, said first and second arms being secured to each other at said proximal ends, said distal end of the first arm having a first grasping portion for contacting an object to be grasped by said tool, and said distal end of the second arm having a second grasping portion for contacting an object to be grasped by said tool;
   an anchoring member positioned over said proximal ends of said first and second arms, said anchoring member having an internal aperture sized and configured to receive the secured proximal ends of said arms; and
   a fiberoptic fiber removably affixed to said anchoring member, said fiberoptic fiber having a proximal end attachable to a light source and a distal end positioned along an outer surface of one of said arms at a location spaced from said grasping portions of said first and second arms such that the fiberoptic fiber transmits light that nonobstructingly illuminates an object adjacent to and graspable between the first grasping portion and the second grasping portion.

2. The illuminable tool of claim 1, wherein the forceps is a surgical forceps.

3. The illuminable tool of claim 2, wherein the surgical forceps is selected from the group consisting of Adson forceps, DeBakey forceps, Neuro forceps, bayonet forceps, jewelers forceps, smooth pickups, and toothed pickups.

4. The illuminable tool of claim 1, wherein the fiberoptic fiber is affixed to an outer face of said one arm.

5. The illuminable tool of claim 1, wherein the fiberoptic fiber is affixed to a top face of said one arm.

6. The illuminable tool of claim 1, wherein the fiberoptic fiber is affixed to a bottom face of said one arm.

7. The illuminable tool of claim 1, wherein the fiberoptic fiber is carried within a light guide assembly.

8. The illuminable tool of claim 1, wherein the anchoring member is removably attached to the forceps.

9. The illuminable tool of claim 1, further comprising a light cable removably attached to the proximal end of the fiberoptic fiber for conveying light energy thereto.

10. The illuminable tool of claim 9, wherein the light cable comprises a fiberoptic cable assembly.

11. The illuminable tool of claim 1, further comprising an anchoring clip that affixes the fiberoptic fiber to the forceps distal to the proximal end of the forceps and proximal to the grasping portion of said one arm.

12. The illuminable tool of claim 1, wherein the fiberoptic fiber passes through a hypotube.

13. The illuminable tool of claim 12, wherein the hypotube is adjustable.

14. The illuminable tool of claim 1, wherein the fiberoptic fiber is disposable.

15. The illuminable tool of claim 1, wherein the fiberoptic fiber is reusable.

16. The illuminable tool of claim 1, further comprising a light adapter for attaching the fiberoptic, fiber to the light source, the light adapter comprising:
  a body having a lumen, a proximal end for connection to the light source and a distal end for connection to the fiberoptic fiber;
  a light transmitting insulator positioned in the proximal end of said light adapter body; and
  a means for anchoring the fiberoptic fiber.

17. The illuminable tool of claim 16, wherein the insulator is glass.

18. The illuminable tool of claim 16, wherein the means for anchoring the fiber optic cable comprises at least one of the following: an iris, set screws, ratchets, adhesives, spring clamps, trumpet valve clamps; roller clamps, cam or lever locks.

19. The illuminable tool of claim 18, wherein the iris is an elastomeric iris.

20. The illuminable tool of claim 16, the light adapter further comprises a heat sink.

21. The illuminable tool of claim 16, wherein the light adapter further comprises a visual indicator to indicate insertion of the fiberoptic fiber.

22. The illuminable tool of claim 16, wherein the light adapter is molded to the fiberoptic fiber.

23. The illuminable tool of claim 16, wherein the light adapter is bonded to the fiberoptic fiber.

24. The illuminable tool of claim 1, wherein the internal aperture of said anchoring member comprises a central slot having a height of about 0.5 inches, and a width of between about 0.050 and 0.090 inches in at least one region.

25. The illuminable tool of claim 24, wherein the internal aperture further comprises an opening in communication with the slot, wherein the opening has a width of about 0.090 inches.

26. The illuminable tool of claim 24, wherein the slot has a distal region and a proximal region, the proximal region having a width smaller than a width of the distal region.

27. The illuminable tool of claim 26, in which the width of the slot decreases in at least one step from the distal region to the proximal region.

28. The illuminable tool of claim 26, wherein the distal region of the slot has a width of about 0.090 inches, and the proximal region of the slot has a width of about 0.050 inches.

29. The illuminable tool of claim 26, wherein the distal region comprises about half of the slot.

30. An illuminable tool comprising:
  forceps having first and second legs secured together at a proximal end, each said leg having an inner surface for engaging an object to be grasped;
  an anchoring base attached to said proximal end of said forceps, said anchoring base including an internal opening sized and configured to receive the proximal end of said forceps; and
  a light guide having a proximal end and a distal end, and comprising a fiberoptic fiber, the light guide being attached to the anchoring base, and the distal end of the light guide being spaced from the first leg and the second leg and being approximately centered between said first and second legs such that said light guide is free of contact with said inner surfaces of said arms.

31. The lighting accessory of claim 30, further comprising a cable assembly connected to the proximal end of the fiberoptic fiber for conveying light energy thereto.

32. The lighting accessory system of claim 30, wherein the anchoring base caps the proximal end of the tool.

33. The lighting accessory system of claim 30, wherein the anchoring base is removably attached to the proximal end of the forceps.

34. The lighting accessory system of claim 30, wherein the light guide further comprises a hypotube, the fiberoptic fiber passing therethrough.

35. The lighting accessory system of claim 34, wherein the hypotube is adjustably positionable between the first leg and the second leg.

36. The lighting accessory system of claim 30, wherein at least one of the anchoring base and the light guide is disposable.

37. The lighting accessory system of claim 30, wherein at least one of the anchoring base and the light guide is reusable.

38. The lighting accessory system of claim 30, wherein at least one of the anchoring base and the light guide is sterilizable.

39. The lighting accessory system of claim 30, further comprising a radio-opaque marker.

40. An illuminable surgical tool comprising:
  a first leg and a second leg joined to each other at a proximal end of the tool;
  an anchoring base having an opening sized and configured to removably receive the proximal ends of said legs, said anchoring base further including an aperture extending therethrough; and
  a fiberoptic fiber connectable to a light source, said fiber optic fiber having a proximal portion passing through the aperture and having a distal portion extending distally to provide illumination to a distal end of the tool, said distal portion of said fiber optic fiber extending along a length of said legs and being free of a direct connection to said legs.

41. The lighting system of claim 40, wherein the anchoring base is elastomeric.

42. The lighting system of claim 40, wherein the tool is a forceps having a first leg and a second leg that are joined to each other at a proximal end of the forceps.

* * * * *

UNITED STATES PATENT AND TRADEMARK OFFICE
CERTIFICATE OF CORRECTION

PATENT NO. : 6,648,902 B2
DATED : November 18, 2003
INVENTOR(S) : Diane L. Colgan It is certified that error appears in the above-identified patent and that said Letters Patent is hereby corrected as shown below:

<u>Title page,</u>
Item [57], ABSTRACT, please replace "stem" with -- system --

Signed and Sealed this

Tenth Day of August, 2004

JON W. DUDAS
*Acting Director of the United States Patent and Trademark Office*